(12) United States Patent
Pesiri

(10) Patent No.: US 7,717,001 B2
(45) Date of Patent: May 18, 2010

(54) APPARATUS FOR AND METHOD OF SAMPLING AND COLLECTING POWDERS FLOWING IN A GAS STREAM

(75) Inventor: David Richard Pesiri, Laguna Beach, CA (US)

(73) Assignee: SDC Materials, Inc., Tempe, AZ (US)

( * ) Notice: Subject to any disclaimer, the term of this patent is extended or adjusted under 35 U.S.C. 154(b) by 800 days.

(21) Appl. No.: 11/246,865

(22) Filed: Oct. 7, 2005

(65) Prior Publication Data

US 2006/0096393 A1 May 11, 2006

Related U.S. Application Data

(60) Provisional application No. 60/617,586, filed on Oct. 8, 2004.

(51) Int. Cl.
*G01N 1/22* (2006.01)

(52) U.S. Cl. .................... 73/863.21; 73/863.41; 95/273; 96/413

(58) Field of Classification Search .................... 96/413; 95/268, 273; 55/320, 468; 73/863.23, 863.21
See application file for complete search history.

(56) References Cited

U.S. PATENT DOCUMENTS

| | | | |
|---|---|---|---|
| 2,419,042 A | 4/1947 | Todd | 202/205 |
| 2,519,531 A | 8/1950 | Worn | 230/95 |
| 2,689,780 A | 9/1954 | Rice | 23/106 |
| 3,001,402 A | 9/1961 | Koblin | 73/421.5 |
| 3,457,788 A | 7/1969 | Miyajima | 73/422 |
| 3,537,513 A | 11/1970 | Austin, et al. | 165/70 |
| 3,741,001 A * | 6/1973 | Fletcher et al. | 73/28.05 |
| 3,774,442 A * | 11/1973 | Gustavsson | 73/28.04 |
| 3,959,420 A | 5/1976 | Geddes et al. | 261/112 |
| 4,008,620 A * | 2/1977 | Narato et al. | 73/864.34 |
| 4,139,497 A | 2/1979 | Castor et al. | |

(Continued)

FOREIGN PATENT DOCUMENTS

JP  56-146804  11/1981

(Continued)

OTHER PUBLICATIONS

Coating Generation: Vaporization of Particles in Plasma Spraying and Splat Formation, M. Vardelle, A. Vardelle, K-I li, P. Fauchais, Universite de Limoges, 123 Avenue A. Thomas 87000, Limoges, F. , pp. 1093-1099.

(Continued)

*Primary Examiner*—Duane Smith
*Assistant Examiner*—Ives Wu
(74) *Attorney, Agent, or Firm*—Haverstock & Owens LLP

(57) ABSTRACT

A device for sampling of a mixture of ultrafine particles within a moving gas stream includes a suction generator, at least one sample collection element, and a conduit structure coupling the sample collection element with the suction generator. In some embodiments, the suction generator is configurable to separate by suction a portion of a gas stream containing a plurality of ultrafine particles, and to entrain with a motive fluid forming an output mixture. In some embodiments, a conduit is configured to accept a gas stream containing ultrafine particles and to channel it to the collection element.

14 Claims, 3 Drawing Sheets

U.S. PATENT DOCUMENTS

Figure 1:
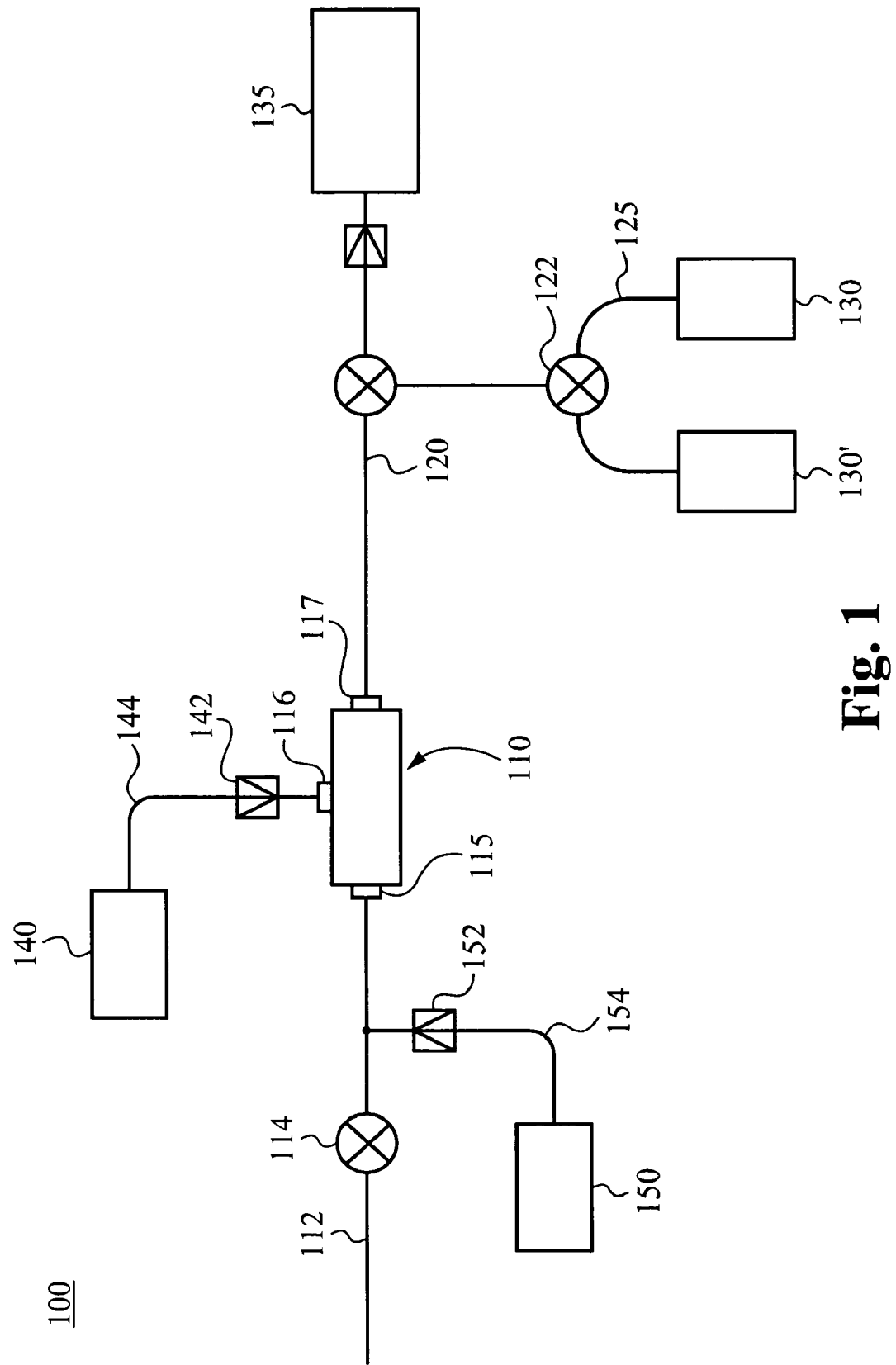

| | | | | |
|---|---|---|---|---|
| 4,171,288 A | 10/1979 | Keith et al. | | |
| 4,388,274 A | 6/1983 | Rourke et al. | | |
| 4,436,075 A | 3/1984 | Campbell et al. | | 123/557 |
| 4,824,624 A | 4/1989 | Palicka et al. | | 264/67 |
| 4,983,555 A | 1/1991 | Roy et al. | | 501/120 |
| 4,987,033 A | 1/1991 | Abkowitz et al. | | 428/469 |
| 5,043,548 A | 8/1991 | Whitney et al. | | 219/121.84 |
| 5,073,193 A | 12/1991 | Chaklader et al. | | 75/346 |
| 5,369,241 A | 11/1994 | Taylor et al. | | 219/121.47 |
| 5,371,049 A | 12/1994 | Moffett et al. | | 501/89 |
| 5,372,629 A | 12/1994 | Anderson et al. | | 75/332 |
| 5,392,797 A | 2/1995 | Welch | | 134/108 |
| 5,439,865 A | 8/1995 | Abe et al. | | |
| 5,485,941 A | 1/1996 | Guyomard et al. | | 222/1 |
| 5,534,149 A | 7/1996 | Birkenbeil et al. | | |
| 5,553,507 A * | 9/1996 | Basch et al. | | 73/863.01 |
| 5,611,896 A | 3/1997 | Swanepoel et al. | | 204/169 |
| 5,630,322 A | 5/1997 | Heilmann et al. | | 62/95 |
| 5,749,938 A | 5/1998 | Coombs | | 75/332 |
| 5,776,359 A | 7/1998 | Schultz et al. | | 252/62.51 |
| 5,788,738 A | 8/1998 | Pirzada et al. | | 75/331 |
| 5,811,187 A | 9/1998 | Anderson et al. | | 428/403 |
| 5,853,815 A | 12/1998 | Muehlberger | | 427/446 |
| 5,905,000 A | 5/1999 | Yadav et al. | | 429/33 |
| 5,935,293 A | 8/1999 | Detering et al. | | 75/10.29 |
| 5,989,648 A | 11/1999 | Phillips | | 427/456 |
| 5,993,967 A | 11/1999 | Brotzman, Jr. et al. | | 428/407 |
| 5,993,988 A | 11/1999 | Ohara et al. | | 429/40 |
| 6,012,647 A | 1/2000 | Ruta et al. | | 239/132.1 |
| 6,033,781 A | 3/2000 | Brotzman, Jr. et al. | | 428/405 |
| 6,059,853 A | 5/2000 | Coombs | | 75/332 |
| 6,102,106 A | 8/2000 | Manning et al. | | 165/76 |
| 6,214,195 B1 | 4/2001 | Yadav et al. | | 205/334 |
| 6,228,904 B1 | 5/2001 | Yadav et al. | | 523/210 |
| 6,254,940 B1 | 7/2001 | Pratsinis et al. | | 427/562 |
| 6,261,484 B1 | 7/2001 | Phillips et al. | | 264/5 |
| 6,267,864 B1 | 7/2001 | Yadav et al. | | 205/341 |
| 6,344,271 B1 | 2/2002 | Yadav et al. | | 428/402 |
| 6,379,419 B1 | 4/2002 | Celik et al. | | 75/346 |
| 6,387,560 B1 | 5/2002 | Yadav et al. | | 429/45 |
| 6,395,214 B1 | 5/2002 | Kear et al. | | 264/434 |
| 6,398,843 B1 | 6/2002 | Tarrant | | 75/249 |
| 6,409,851 B1 | 6/2002 | Sethuram et al. | | 148/565 |
| 6,416,818 B1 | 7/2002 | Aikens et al. | | 427/383.1 |
| RE37,853 E | 9/2002 | Detering et al. | | 75/10.19 |
| 6,444,009 B1 | 9/2002 | Liu et al. | | 75/332 |
| 6,517,800 B1 | 2/2003 | Cheng et al. | | 423/447.1 |
| 6,524,662 B2 | 2/2003 | Jang et al. | | 427/535 |
| 6,531,704 B2 | 3/2003 | Yadav et al. | | 250/493.1 |
| 6,554,609 B2 | 4/2003 | Yadav et al. | | 432/9 |
| 6,562,495 B2 | 5/2003 | Yadav et al. | | 429/12 |
| 6,569,397 B1 | 5/2003 | Yadav et al. | | 423/345 |
| 6,569,518 B2 | 5/2003 | Yadav et al. | | 428/323 |
| 6,572,672 B2 | 6/2003 | Yadav et al. | | 75/343 |
| 6,607,821 B2 | 8/2003 | Yadav et al. | | 428/323 |
| 6,610,355 B2 | 8/2003 | Yadav et al. | | 427/115 |
| 6,635,357 B2 | 10/2003 | Moxson et al. | | 428/548 |
| 6,641,775 B2 | 11/2003 | Vigliotti et al. | | 264/618 |
| 6,652,822 B2 | 11/2003 | Phillips et al. | | 423/290 |
| 6,652,967 B2 | 11/2003 | Yadav et al. | | 428/403 |
| 6,669,823 B1 | 12/2003 | Sarkas et al. | | 204/164 |
| 6,682,002 B2 * | 1/2004 | Kyotani | | 239/318 |
| 6,689,192 B1 | 2/2004 | Phillips et al. | | 75/342 |
| 6,699,398 B1 | 3/2004 | Kim | | 216/55 |
| 6,706,097 B2 | 3/2004 | Zornes | | 96/153 |
| 6,713,176 B2 | 3/2004 | Yadav et al. | | 428/402 |
| 6,716,525 B1 | 4/2004 | Yadav et al. | | 428/402 |
| 6,746,791 B2 | 6/2004 | Yadav et al. | | 429/30 |
| 6,772,584 B2 | 8/2004 | Chun et al. | | 60/275 |
| 6,786,950 B2 | 9/2004 | Yadav et al. | | 75/346 |
| 6,813,931 B2 | 11/2004 | Yadav et al. | | 73/31.05 |
| 6,817,388 B2 | 11/2004 | Tsangaris et al. | | 141/82 |
| 6,832,735 B2 | 12/2004 | Yadav et al. | | 241/16 |
| 6,838,072 B1 | 1/2005 | Kong et al. | | 423/594.2 |
| 6,855,426 B2 | 2/2005 | Yadav | | 428/403 |
| 6,855,749 B1 | 2/2005 | Yadav et al. | | 523/105 |
| 6,886,545 B1 | 5/2005 | Holm | | 123/568.21 |
| 6,896,958 B1 | 5/2005 | Cayton et al. | | 428/323 |
| 6,902,699 B2 | 6/2005 | Fritzemeier et al. | | 419/38 |
| 6,916,872 B2 | 7/2005 | Yadav et al. | | 524/430 |
| 6,919,527 B2 | 7/2005 | Boulos et al. | | 219/121.52 |
| 6,933,331 B2 | 8/2005 | Yadav et al. | | 523/210 |
| 6,986,877 B2 | 1/2006 | Takikawa et al. | | 423/447.3 |
| 6,994,837 B2 | 2/2006 | Boulos et al. | | 423/613 |
| 7,007,872 B2 | 3/2006 | Yadav et al. | | 241/1 |
| 7,052,777 B2 | 5/2006 | Brotzman, Jr. et al. | | 428/570 |
| 7,073,559 B2 | 7/2006 | O'Larey et al. | | 164/76.1 |
| 7,081,267 B2 | 7/2006 | Yadav | | 427/115 |
| 7,101,819 B2 | 9/2006 | Rosenflanz et al. | | 501/10 |
| 7,147,544 B2 | 12/2006 | Rosenflanz | | 451/28 |
| 7,147,894 B2 | 12/2006 | Zhou et al. | | 427/256 |
| 7,166,198 B2 | 1/2007 | Van Der Walt et al. | | 204/165 |
| 7,166,663 B2 | 1/2007 | Cayton et al. | | 524/430 |
| 7,172,649 B2 | 2/2007 | Conrad et al. | | 106/35 |
| 7,178,747 B2 | 2/2007 | Yadav et al. | | 241/23 |
| 7,208,126 B2 | 4/2007 | Musick et al. | | 423/69 |
| 7,211,236 B2 | 5/2007 | Stark et al. | | 423/592.1 |
| 7,217,407 B2 | 5/2007 | Zhang | | 423/610 |
| 7,220,398 B2 | 5/2007 | Sutorik et al. | | |
| 7,307,195 B2 | 12/2007 | Polverejan et al. | | 585/443 |
| 7,323,655 B2 | 1/2008 | Kim | | 219/121.43 |
| 7,384,447 B2 | 6/2008 | Kodas et al. | | 75/332 |
| 2002/0068026 A1 | 6/2002 | Murrell et al. | | |
| 2002/0079620 A1 | 6/2002 | Dubuis et al. | | 264/328.14 |
| 2003/0036786 A1 | 2/2003 | Duren et al. | | 607/96 |
| 2003/0066800 A1 | 4/2003 | Saim et al. | | |
| 2003/0108459 A1 | 6/2003 | Wu et al. | | 422/186.04 |
| 2003/0223546 A1 | 12/2003 | McGregor et al. | | 378/143 |
| 2004/0023453 A1 | 2/2004 | Xu et al. | | |
| 2004/0103751 A1 | 6/2004 | Joseph et al. | | 75/10.19 |
| 2004/0167009 A1 | 8/2004 | Kuntz et al. | | 501/95.2 |
| 2004/0251017 A1 | 12/2004 | Pillion et al. | | 165/289 |
| 2005/0000321 A1 | 1/2005 | O'Larey et al. | | 75/952 |
| 2005/0000950 A1 | 1/2005 | Schroder et al. | | 219/121.59 |
| 2005/0077034 A1 | 4/2005 | King | | 165/163 |
| 2005/0097988 A1 | 5/2005 | Kodas et al. | | 75/332 |
| 2005/0220695 A1 | 10/2005 | Abatzoglou et al. | | |
| 2005/0233380 A1 | 10/2005 | Pesiri et al. | | 435/7.1 |
| 2005/0240069 A1 | 10/2005 | Polverejan et al. | | 585/444 |
| 2005/0258766 A1 | 11/2005 | Kim | | 315/111.21 |
| 2006/0051505 A1 | 3/2006 | Kortshagen et al. | | 427/212 |
| 2006/0068989 A1 | 3/2006 | Ninomiya et al. | | |
| 2006/0096393 A1 | 5/2006 | Pesiri | | 73/863.21 |
| 2006/0105910 A1 | 5/2006 | Zhou et al. | | |
| 2006/0108332 A1 | 5/2006 | Belashchenko | | 219/121.47 |
| 2006/0159596 A1 | 7/2006 | De La Veaux et al. | | 422/151 |
| 2006/0231525 A1 | 10/2006 | Asakawa et al. | | 216/56 |
| 2007/0063364 A1 | 3/2007 | Hsiao et al. | | 264/5 |
| 2007/0084308 A1 | 4/2007 | Nakamura et al. | | 75/346 |
| 2007/0084834 A1 | 4/2007 | Hanus et al. | | 219/121.5 |
| 2007/0087934 A1 | 4/2007 | Martens et al. | | 502/214 |
| 2007/0173403 A1 | 7/2007 | Koike et al. | | |

FOREIGN PATENT DOCUMENTS

| | | |
|---|---|---|
| WO | WO 02/092503 A1 | 11/2002 |
| WO | 2004052778 A2 | 6/2004 |
| WO | WO 2006/079213 A1 | 8/2006 |

OTHER PUBLICATIONS

J. Heberlein, "New Approaches in Thermal Plasma Technology", Pure Appl. Chem., vol. 74, No. 3, 2002, pp. 327-335.

T. Yoshida, "The Future of Thermal Plasma Processing for Coating", Pure & Appl. Chem., vol. 66, No. 6, 1994 pp. 1223-1230.

A. Gutsch et al., "Gas-Phase Production of Nanoparticles", Kona No. 20, 2002, pp. 24-37.

Dr. Heike Mühlenweg et al., "Gas-Phase Reactions—Open Up New Roads to Nanoproducts", Degussa ScienceNewsletter No. 08, 2004, pp. 12-16.

H. Konrad et al., "Nanostructured Cu-Bi Alloys Prepared by Co-Evaporation in a Continuous Gas Flow," NanoStructured Materials, vol. 7, No. 6, Apr. 1996, pp. 605-610.

M.Vardelle et al., "Experimental Investigation of Powder Vaporization in Thermal Plasma Jets," Plasma Chemistry and Plasma Processing, vol. 11, No. 2, Jun. 1991, pp. 185-201.

P. Fauchais et al., "Plasma Spray: Study of the Coating Generation," Ceramics International, Elsevier, Amsterdam, NL, vol. 22, No. 4, Jan. 1996, pp. 295-303.

P. Fauchais et al., "Les Dépôts Par Plasma Thermique," Revue Generale De L'Electricitie, RGE. Paris, FR, No. 2, Jan. 1993, pp. 7-12.

P. Fauchais et al, "La Projection Par Plasma: Une Revue," Annales De Physique, vol. 14, No. 3, Jun. 1989, pp. 261-310.

China Patent Agent (H.K) Ltd., Foreign Office Action dated Aug. 7, 2009, Code No. 5433 Chinese Patent Application No. 2005/80042357.5, Application Dated: Oct. 7, 2005, Applicant: SDC Materials, LLC.

Kenvin et al. "Supported Catalysts Prepared from Monouclear Copper Complexes: Catalytic Properties", Journal of Catalysis, pp. 81-91.

National Aeronautics and Space Administration, "Enthalpy", http://www.grc.nasa.gov/WWW/K-12/airplane/enthalpy.html, Nov. 23, 2009, 1 page.

* cited by examiner

APPARATUS FOR AND METHOD OF SAMPLING AND COLLECTING POWDERS FLOWING IN A GAS STREAM

CROSS-REFERENCE TO RELATED APPLICATIONS

This application claims priority under 35 U.S.C. §119(e) to co-pending U.S. Provisional Patent Application No. 60/617,586 filed Oct. 8, 2004, which is hereby incorporated by reference.

FIELD OF THE INVENTION

This invention relates to the field of powder sampling and more specifically a process of and apparatus for separating and collecting an ultrafine power from a flowing gas stream.

BACKGROUND OF THE FIELD OF THE INVENTION

Sampling particles from a gas stream presents several challenges. Traditional sampling methods are ill suited to the collection of vapor phase ultrafine particles. Many powders possess properties that lead to agglomeration and clogging in small features and narrow apertures. Due to their small size, ultrafine powders with effective diameters below 100 nanometers are subject to being acted upon by of even the slightest intermolecular forces. This generally such powders very difficult to handle and convey, and gives them a strong tendency to agglomerate with one another, and to adhere to surfaces and to small dimensions within mechanical devices.

These challenges must be confronted in the design of devices for sampling fine powders.

SUMMARY OF THE DISCLOSURE

A device samples and collects particles that are moving in a gas stream. A process acts on a gas stream containing particles, sampling and collecting particles from the gas stream. Generally, the device and process of the present invention employ suction to separate a particle-containing portion of a gas stream, and then collect particles by using collection elements, e.g. filters, containers, or some combination. In an exemplary configuration, a vacuum pump pulls the particle-containing portion through a filter element. In another exemplary configuration, another type of suction generator directs the particle-containing portion into a selected collection element containing a filter.

In a first aspect, the device of the present invention includes means for channeling a motive fluid coupled with a conduit, and means for cleaning the means for channeling and the conduit configured therewithin.

The means for channeling is configured for separating a selected particle-containing portion of the gas stream and entraining the particle-containing portion into a motive fluid-particle mixture. When the device is positioned within a gas stream, the means for channeling provides a force sufficient to separate a portion of the gas stream. Further, the conduit is coupled with the means for channeling, and capable of distributing the motive fluid-particle mixture into a selected collection element. The means for cleaning is configured to remove a residue from within the means for channeling and the conduit.

In one mode, operation of the device includes only a few steps. The device is coupled with a conduit or other structure containing a moving gas stream having particles therein. Motive fluid flows through the means for channeling, which separates a selected particle-containing portion from the gas stream and forms a motive fluid-particle mixture. The motive fluid-particle mixture flows from the means for channeling through the conduit. Flowing the motive fluid-particle mixture through the means for channeling and the conduit activates the means for cleaning, which is configured to remove residue from within the means for channeling and the conduit. The conduit is configured to distribute a portion of the motive fluid-particle mixture into a selected collection element.

In a further embodiment, the present invention discloses a device for sampling of a mixture of ultrafine particles from within a moving gas stream. The device comprises a suction generator, configurable to separate by suction and to entrain with a motive fluid, forming an output mixture, a portion of a gas stream containing a plurality of ultrafine particles, a conduit structure to channel the output mixture, and at least one sample collection element configurable to accept a selected portion of the output mixture, and coupled with the suction generator via the conduit structure.

In the preferred embodiment, the device further comprises a sweep fluid reservoir and a motive fluid reservoir. In addition, the suction generator is preferably a Venturi-type eductor having a motive fluid inlet, a suction inlet, and an outlet. The sweep fluid reservoir is coupled with the suction generator and configured to deliver sweep fluid therethrough without forming suction therein, while the motive fluid reservoir is configured to deliver motive fluid through the motive fluid inlet to the outlet, forming suction within the suction inlet.

In another aspect of the present invention, an apparatus for separating a portion of a moving mixture of ultrafine particles from a gas stream is presented. The apparatus includes a suction generator configured to entrain a particle-containing portion of a moving mixture within a motive fluid to form an output mixture, a sweep fluid reservoir coupled with the suction generator and configured to deliver a sweep fluid therethrough, and one or more collection elements removably coupled with the outlet to receive selected portions of the output-mixture. The suction generator is preferably configured to allow removal, by the sweep fluid and by the output mixture, of a residue from there within. The collection elements can comprise filter elements.

Preferably, the suction generator is sealable from the moving mixture. Also, the apparatus preferably includes a motive fluid reservoir configured to deliver motive fluid to the suction generator, whereby suction is generated within the suction generator. More preferably, the motive fluid reservoir and the sweep fluid reservoir are configured to irreversibly deliver their respective fluids. The residue removed from within the suction generator is preferably a residue deposited from a prior output mixture during a prior use.

In a further aspect, the present intention presents an apparatus for separating a portion of a moving mixture of ultrafine particles within a gas stream. The apparatus comprises a Venturi-type eductor valve having a motive fluid inlet, a suction inlet, and an outlet, a motive fluid reservoir coupled with the motive fluid inlet, a sweep fluid reservoir coupled with the suction inlet, a conduit structure coupled with the outlet, and one or more collection elements sealably coupled with the conduit structure. The Venturi-type eductor valve is configured to form a negative pressure stream biased from the suction inlet to the outlet when motive fluid is flowed from the motive fluid inlet to the outlet. The negative pressure stream formed is capable of entraining a portion of the moving mixture of ultrafine particles within a gas stream. The suction inlet is configurable to communicate with the moving mixture of ultrafine particles within a gas stream.

Further, the motive fluid reservoir is configured to irreversibly deliver motive fluid through the motive fluid inlet and the sweep fluid reservoir is configured to irreversibly deliver sweep fluid through the suction inlet to the outlet. The conduit coupling the conduit structure with the one or more collection elements is preferably configured to allow the removal of a residue from within the conduit structure by the output mixture and by the sweep fluid. The one or more collection elements are configured to accept delivery of at least a portion of the output mixture. At least one of the collection elements is a bulk collection chamber coupled with the conduit structure via a one way valve biased to allow flow only from the conduit structure into the bulk collection chamber. The collection elements can comprise filter elements.

Also within the present invention, a method of sampling powder from a gas stream which contains ultrafine particles is presented. The method comprises the steps of separating a portion of gas containing a target powder from the gas stream by suction to form a mixture of a motive fluid with the target powder entrained therein, directing a first portion of the mixture through a conduit structure for a period of time sufficient to substantially clean the conduit structure, and directing a second portion of the mixture through the conduit structure into a collection element after the period of time.

Preferably, the suction is provided by a negative pressure stream formed by flowing the motive fluid through a Venturi-type eductor. Further, a step of flowing a sweep fluid through the conduit structure to maintain substantial entrainment of the target powder is preferably included. Alternatively, the suction is provided by a vacuum generator, e.g. a vacuum pump, a standard vacuum cleaner. In some embodiments, the collection element comprises a filter, and in some embodiments the collection element comprises a vessel.

In the preferred step of the present invention, the method of sampling powder from a gas stream is repeated. Specifically the steps of 'flowing' through the step of 'directing a second portion' are repeated, operating on preferably different target powders. In this application, any residue left within the conduit structure by a given target powder is substantially cleaned from the conduit structure during sampling of a subsequent target powder by the step of 'directing a first portion' before the second portion of the subsequent target powder is collected.

In a further aspect, the present invention presents a process for achieving high purity sampling of at least two mixtures from a single source. The process comprises two sets of similar steps, each set operating on a preferably different target mixture. The first set includes the following steps: flowing a motive fluid through a Venturi-type eductor valve to form a negative pressure stream, applying the negative pressure stream to a first gas stream to separate a portion thereof and entrain it into a first target mixture, the gas stream containing a first target powder and originating from a source, and directing the first target mixture through a conduit network into a first collection element. Prior to the second set of steps, an intermediate clean up step of flowing a sweep gas through the Venturi-type eductor valve, without forming a negative pressure stream, and through the conduit network to remove at least a portion of remaining first target mixture therefrom, is performed. The second set includes the following steps: flowing a motive fluid through a Venturi-type eductor valve to form a negative pressure stream, applying the negative pressure stream to a second gas stream to separate a portion thereof and entrain it into a second target mixture, the gas stream containing a second target powder and originating from the source, flowing a portion of the second target mixture through the conduit network for a time sufficient to substantially clean the conduit network of the remaining first target mixture, and directing a further portion of the second target mixture through the conduit network into a second collection element.

In the preferred application of the present invention, the process is repeated using additional mixtures, each of which can be unique. This repetition results in the collection of a plurality of high-purity samples of possibly unique materials, without cross-contamination among the samples. Further, in the preferred embodiment, the steps of 'flowing a motive fluid' and of 'flowing a sweep gas' are coordinated to maintain substantial entrainment of the first and the second target powders throughout the conduit network for the duration of the process. This coordination minimizes deposition of target powders within the conduit and the Venturi-type eductor used in the present invention.

The present invention is designed to sample entrained powders produced via gas phase production means, including inert gas condensation, pulsed laser ablation, spark discharge, ion sputtering, chemical vapor synthesis, spray pyrolysis, laser pyrolysis/photothermal synthesis, thermal plasma synthesis, flame synthesis, flame spray pyrolysis, and low temperature reactive synthesis.

DESCRIPTION OF THE SEVERAL DRAWINGS

FIG. 1 is a schematic view of the apparatus of the present invention.

FIG. 2 is a cross-sectional view of the Venturi-type eductor used in the present invention.

FIG. 3 is an illustration of a fluid supply system as included in the present invention.

FIG. 4 is a flow chart illustrating the method of the present invention.

DETAILED DESCRIPTION

The following description is presented to enable one of ordinary skill in the art to make and use the invention. Various modifications to the described embodiments will be readily apparent to those skilled in the art and the generic principles herein may be applied to other embodiments. Thus, the present invention is not intended to be limited to the embodiment shown but is to be accorded the widest scope consistent with the principles and features described herein.

Referring now to FIG. 1, the apparatus 100 is illustrated. Generally, the apparatus 100 includes the suction generator 110, coupled through the conduit structure 120 with the collection elements 130 and 130'. The motive fluid reservoir 140 coupled with the suction generator 110, is one exemplary means of providing a motive fluid and suction generating power to the suction generator 110.

The suction generator 110 includes a suction inlet 115, a motive fluid inlet 116 and a outlet 117. As illustrated, the sample conduit 112 is coupled with the suction inlet 115, the motive fluid reservoir 140 is coupled with the motive fluid inlet 116, and the outlet 117 is coupled with the conduit structure 120.

Suction generated by the suction generator 110 at the suction inlet 115 is applied through the sample conduit 112 to a powder source (not illustrated) which includes powder flowing within a gas stream. The suction generated separates a portion of powder-containing gas from the powder source and moves it through the suction inlet 115. Within the suction generator 110, the powder-containing portion is entrained within a motive fluid. Preferably, the motive fluid is supplied through the motive fluid inlet 116 from the motive fluid reservoir 140. The suction generator 140 then delivers an output mixture comprising an entrained powder to the outlet 117. From the outlet 117, the coupled conduit structure 120 delivers the output mixture to a selected location. Preferably, as illustrated, the conduit structure 120 includes a plurality of valve structures 122 for routing the output mixture to a location selected from a plurality of possible locations. Within the present invention, possible selected locations include the sample collection elements 130, 130' and the bulk collection chamber 135.

In the methods of using the apparatus 100 embodying the present invention, discussed in more detail elsewhere, a portion of the output mixture is delivered from the outlet 117 through the conduit structure 120 to the bulk collection chamber 135 for a selected period of time to clean the conduit structure 120, the suction generator 110 and the sample conduit 112. Following the cleaning step, a further portion of the output mixture is delivered from the outlet 117 through the conduit structure 120 to a selected sample collection element 130'. Once one such sample is collected, the apparatus 100 can be used to collect further samples. For example, the above-described steps may be repeated, operating on a different powder containing gas but in this case selecting the sample collection element 130 and depositing a sample therein. The construction of the apparatus 100 of the present invention is such that using this method to repeatedly sample a plurality of unique materials will not result in cross contamination among the samples, so long as each is deposited in a unique sample collection element. The sample collection elements 130 and 130' can comprise filter elements, vessels, or some combination. For example, in one embodiment, the collection element 130 is a vessel containing a high efficiency particulate air (HEPA) filter, and the collection element 130' is a HEPA filter coupled to a vacuum chamber.

Still referring to FIG. 1, additional aspects of the apparatus 100 are illustrated. Preferably, the motive fluid reservoir 140 is coupled with the motive fluid inlet 116 via the conduit 144, containing a one way valve 142. The one way valve 142 is configured to allow delivery of motive fluid only from the motive fluid reservoir 140 to the motive fluid inlet 116 and not in any other direction. Further, the apparatus 100 preferably comprises the sweep fluid reservoir 150, coupled to the sample conduit 112 by the conduit 154 and thereby with the suction inlet 115 of the suction generator 110. As illustrated, the conduit 154 includes the one way valve 152 configured to allow flow of the sweep fluid only in a direction from the sweep fluid reservoir 150 to the sample conduit 112. The sample conduit 112 preferably includes the valve structure 114, configurable to seal the sample conduit 112 from the powder source.

In operation of the apparatus 100, described briefly above and more thoroughly elsewhere, the sweep fluid reservoir is preferably employed to maintain entrainment of any excess powder following collection. More specifically, once collection is accomplished as described above, motive fluid continues to flow from the motive fluid reservoir 140 while the selected collection element 130' is sealed from the conduit structure using one of the valve structures 122. Thus, though collection has already been performed, entrainment is maintained (however briefly) by the continued flow of motive fluid. Preferably, the flow of motive fluid is temporarily interrupted while a flow of sweep fluid is initiated from the sweep fluid reservoir 150. These steps are performed to maintain substantial entrainment of powder remaining within the apparatus 100 following collection. Preferably, the flow of sweep fluid is directed into the bulk collection chamber 135, substantially purging the sample conduit 112, suction generator 110 and conduit structure 120 of motive fluid and of powder.

Figure 2:
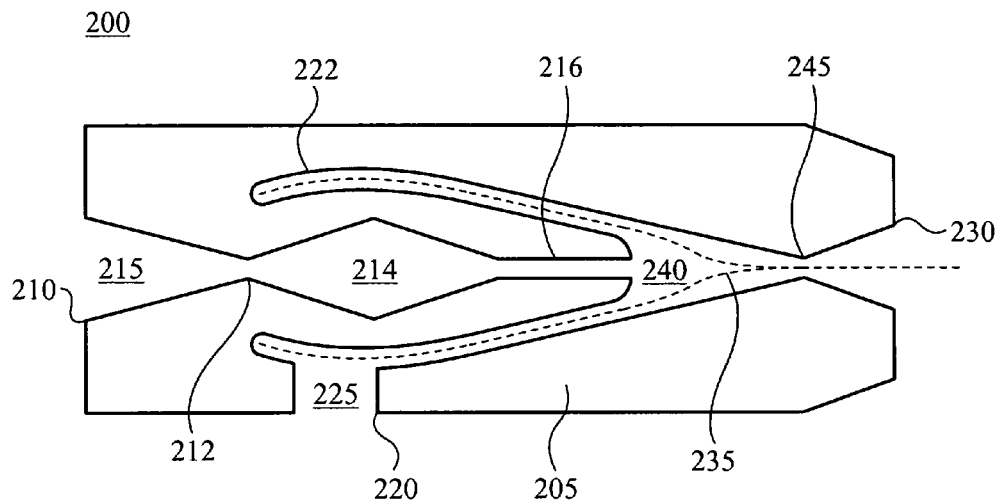

Referring now to FIG. 2, an exemplary embodiment of a suction generator as used in the present invention is described in detail. The exemplary suction generator is a Venturi-type eductor 200, also known by many other names, including the following: aspirator, vacuum generator, mixing tee, Venturi vacuum pump, and sampling jet. Each of these terms describes a type of pump which operates by exploiting the Bernoulli principle. The Bernoulli principle states that the pressure exerted by a fluid on a given surface will decrease as fluid velocity relative to that surface increases. Venturi-type eductors, and equivalent devices, include features therein which constrict fluid flow and thereby increase fluid velocity, creating a pressure differential.

Regardless of the actual principles involved, the Venturi-type eductor 200 includes the eductor body 205, containing the motive fluid inlet 210 and the outlet 230. The motive fluid inlet 210 comprises a cone shaped nozzle, which narrows from a relatively wide opening at an outer surface of the eductor body 205 to a narrow aperture 212. Through a narrow aperture 212 is the nozzle 214 leading to a narrow channel 216, which communicates with the outlet 230 and forms the only point of egress from the motive fluid inlet 210. Fluid 215 passes through motive fluid inlet 210 and then passes through the narrow channel 214 and, if provided at a uniform rate to the motive fluid inlet 210, is thus accelerated.

This design results in the ejection of the fluid 215 at a relatively higher velocity from the narrow channel 216 through the mixing chamber 240 toward the outlet 230. The inertia of the fluid 215, combined with the narrowing construction of the junction 245 create suction between the mixing chamber 240 and the outlet 230. Because the narrowing contours of the junction 245 are smoothly varying and designed to induce minimal turbulence within the fluid 215, laminar acceleration of the fluid 215 is enhanced. Thus injection of the fluid 215 forms a negative pressure stream biased from the mixing chamber 240 to the outlet 230.

The suction inlet 220 is coupled through the eductor body 205 with the mixing chamber 240 to communicate fluidly therewith. The suction inlet 220 connects with the suction chamber 222 which forms a funnel-shaped void within the eductor body 205, narrowing to join the mixing chamber 240. As described above, a negative pressure stream biased from the mixing chamber 240 to the outlet is formed by forcing the fluid 215 into the motive fluid inlet 210. This pressure stream extends through the mixing chamber 240, the suction chamber 222 and out of the suction inlet 220. This negative pressure stream biased from the suction inlet 220 to the outlet 230 is alternately viewed as a suction force capable of pulling available material into the suction inlet 220 and toward the outlet 230.

In the present invention an additive fluid 225 is presented to the suction inlet 220. When the fluid 215 is forced through the motive fluid inlet 210 to the outlet 230, the negative pressure stream biased from the suction inlet 220 to the outlet 230 pulls the additive fluid 225 into the mixing chamber 240 where it admixes to the fluid 215 to form the output mixture 235, which is ejected from the outlet 230.

Preferably, as described in more detail elsewhere, the present invention is used to separate a portion of a moving gas mixture containing a target powder. The suction chamber 222, mixing chamber 240, nozzle 214 and other portions of the Venturi-type eductor are preferably formed to provide sufficient suction to accomplish this task. The particles of the target powder included within the additive fluid 225 are carried along with the fluid and into the suction chamber 222 and subsequently the mixing chamber 240 where as the additive fluid mixes with the fluid 215 to form the output fluid 235, the particles are entrained into the output fluid 235 and carried along therewith. Further, the design of the mixing chamber 240 and the narrow channel 216 is such that substantially zero particles are introduced into the narrow channel 216.

Figure 3:
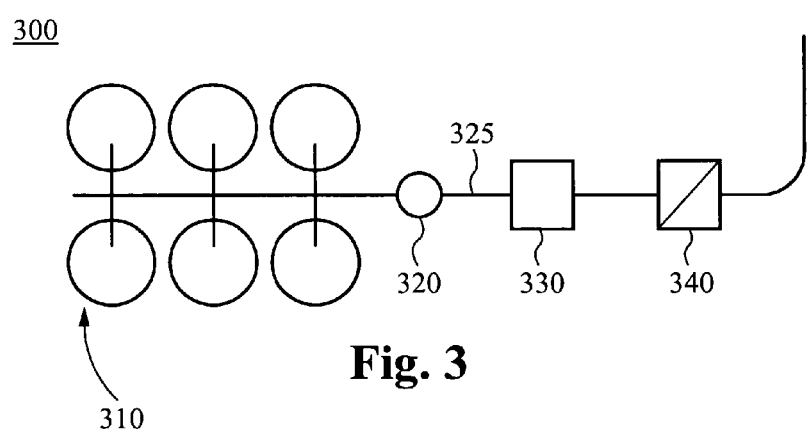

Referring now to FIG. 3, an exemplary fluid supply system 300, having a preferred construction of both the supply of motive fluid and that of sweep fluid within the present invention, is illustrated. The fluid supply system 300 includes a plurality of fluid supply reservoirs 310. Though in the preferred embodiment, these multiple reservoirs all contain a common fluid, it is within the scope of the present invention for multiple fluids to be contained therein, to allow for a variety of applications without need for refitting. For example, in the case of motive fluid supply, one motive fluid well-suited for suction of particles having sizes on the scale of tens of nanometers could be included as well as another motive fluid better-suited for suction of particles having sizes on the scale of hundreds of nanometers. In any case, the fluid flow control system 320 is preferably coupled with the plurality of reservoirs 310 to control both the presence and velocity of flow therefrom. Additionally, the fluid flow control system 320 selects which reservoir from which fluid is flowed during a given time period. From the fluid flow control system 320, fluid is channeled by the conduit 325 toward a selected destination, and preferably through a plurality of conditioning devices. In the illustrated embodiment these conditioning devices include a dehumidifier 330 and particle filter 340.

It is desirable in both the case of sweep fluid and of motive fluid to limit the presence of particles therewithin and to dehumidify the fluid. The motive fluid is channeled through the narrowing nozzle and to form the suction used in device operation. However, as is also described more fully elsewhere, the sweep fluid maintains entrainment of powders and to thus contribute to cleanliness of the apparatus of the present invention. Humidity in powder-gas mixtures, though just one of many contributing factors, usually leads to increased agglomeration of powders and subsequent precipitation from the gas mixture; hence, changes in humidity are preferably avoided in the present invention and the sweep fluid is preferably dehumidified. Changes, abrupt or otherwise, within particle makeup within powder-gas mixtures can similarly result in increased agglomeration and other undesirable outcomes and are thus also preferably avoided in the present invention.

Referring again to FIG. 1, the method of the present invention is discussed. Generally, the present invention relates to a method of sampling powder from a gas stream containing ultrafine particles. The method will be discussed with reference to an exemplary sampling apparatus 100, but is intended only as a general representative separation system. The method comprises a step of separating a portion of gas containing a target powder from the gas stream by suction to form a mixture of a motive fluid with the target powder entrained therein. In the exemplary apparatus 100, this step can include several substeps. In one substep, suction is created within the suction generating device 110. In the exemplary apparatus 100 the suction generating device is understood to be a Venturi-type eductor, similar to the device described above with reference to FIG. 2; however, other suction generating means are contemplated within the present invention, including but not limited to electromechanical pumps and vacuum pumps. In the suction generator 110, a motive fluid is flowed from the motive fluid reservoir 140 through the suction generating device 110 to the outlet 117 forming suction at the suction inlet 115. In an additional substep, the suction generated is applied to a main gas stream containing a target powder, in this case through the sample conduit 112, coupled with the suction inlet 115. Exposure can be implicit in the generation of the suction, or the suction can be generated and then the gas stream exposed thereto by opening a valve or some similar device.

In further steps, the method of the present invention includes a step of directing a first portion of the mixture from the outlet 117 through a conduit structure 120 for a period of time sufficient to substantially clean the conduit structure 120. Preferably, the first portion is diverted by the conduit structure 120 and through the branch 125 thereof which is coupled to the collection element 130, but not actually into a collection element 130. Then, in a subsequent step, a second portion of the mixture is directed through the conduit structure 117 into the collection element 130 after the period of time. Preferably, there is substantially no interruption of flow between the first and second portion and the collection element 130 is simply moved to block the flow and collect the second portion. Therefore, since the first portion has substantially cleaned the conduit structure of any residue, the second portion comprises only the carrier gas of the gas stream, the target powder, and the motive fluid used to generate suction (in the case of a Venturi type suction generator).

Further steps are preferably included. Specifically, a step of flowing a sweep fluid through the suction generator 110 and the conduit structure 120 from a sweep fluid reservoir 150 to maintain substantial entrainment of the target powder. This step is preferably performed following the collection of the second portion of the mixture to maintain entrainment of any remaining powder within the apparatus 100 and preferably delivers the remaining powder into the bulk collection chamber 135. This step is advantageous when the process is repeated, using different mixtures which include different target powders. This repetition is preferably included within the method of the present invention. Repetition of the steps of 'flowing' through the step of 'directing a second portion', followed by the step of 'flowing a sweep fluid' allows the sampling of discrete quantities of multiple target powders without intermixture or cross contamination among the samples.

Figure 4:
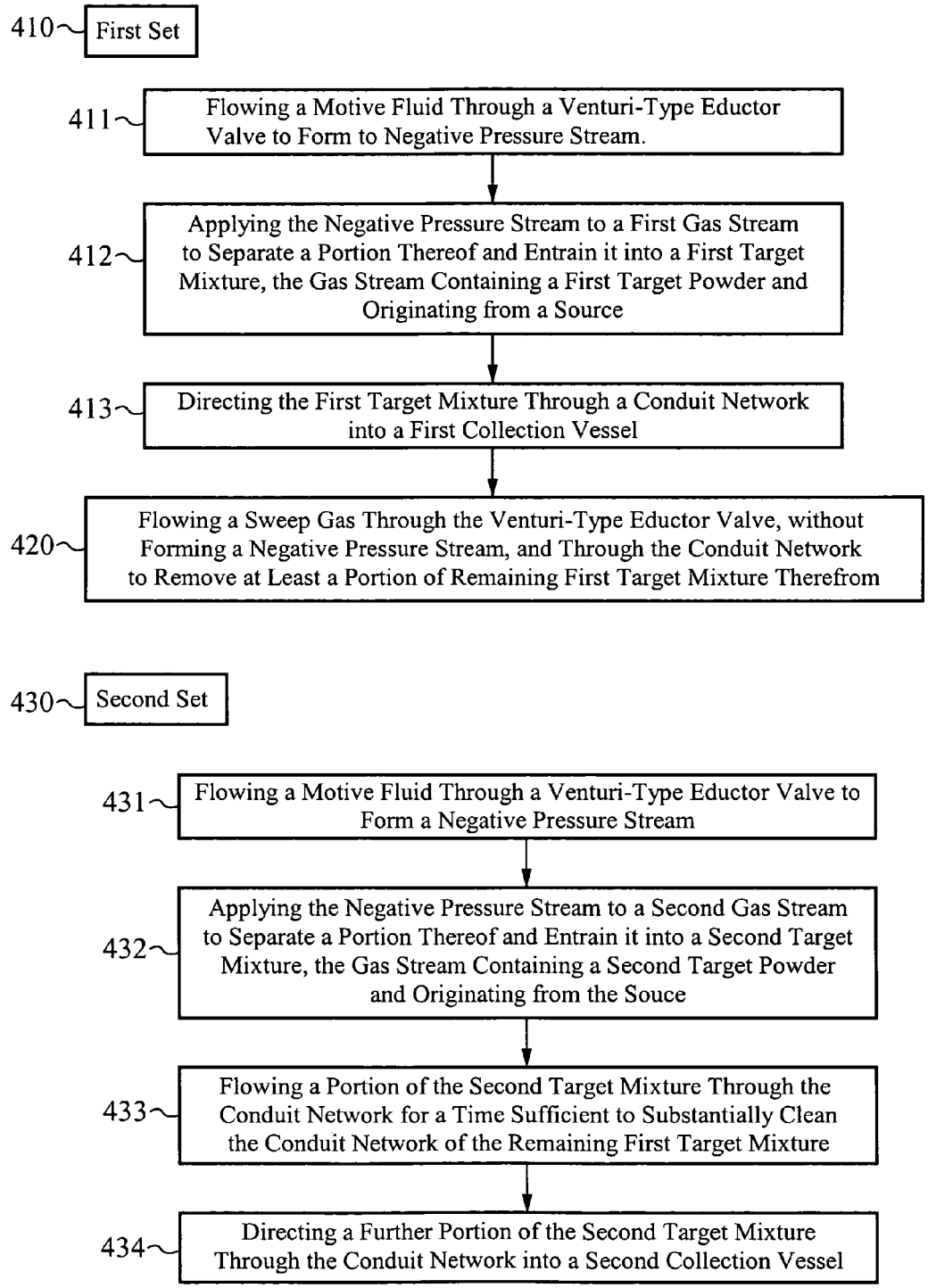

Referring now to FIG. 4, a process for achieving high purity sampling of at least two mixtures from a single source, as contemplated within the present invention is show in flow chart form. The process includes two sets of similar steps and one intermediate step. The first set 410 includes the step 411 of flowing a motive fluid through a Venturi-type eductor valve to form a negative pressure stream, the step applying the negative pressure stream to a first gas stream to separate a portion thereof and entrain it into a first target mixture, the gas stream containing a first target powder and originating from a source, the step 412 of directing the first target mixture through a conduit network into a first collection element. In the intermediate step 420, a sweep gas is flowed through the Venturi-type eductor valve, without forming a negative pressure stream, and through the conduit network to remove at least a portion of remaining first target mixture therefrom. The second set 430 includes the steps 431 of flowing a motive fluid through a Venturi-type eductor valve to form a negative pressure stream, 432 of applying the negative pressure stream to a second gas stream to separate a portion thereof and entrain it into a second target mixture, the gas stream containing a second target powder and originating from the source, 433 of flowing a portion of the second target mixture through the conduit network for a time sufficient to substantially clean the conduit network of the remaining first target mixture, and 434 of directing a further portion of the second target mixture through the conduit network into a second collection element.

Preferably, the steps 411 and 431 of 'flowing a motive fluid' and the step 420 of 'flowing a sweep gas' are coordinated to maintain substantial entrainment of the first and the second target powders throughout the conduit network for the duration of the process.

The present invention has been described in terms of specific embodiments incorporating details to facilitate the understanding of the principles of construction and operation of the invention. As such, references herein to specific embodiments and details thereof are not intended to limit the scope of the claims appended hereto. It will be apparent to those skilled in the art that modifications can be made to the embodiments chosen for illustration without departing from the spirit and scope of the invention.

What is claimed is:

1. A device for sampling and collecting particles from a gas stream, comprising:
   a. means for channeling a motive fluid and for separating a selected particle-containing portion of a gas stream and entraining the particle-containing portion into a motive fluid-particle mixture;
   b. a conduit to distribute the motive fluid-particle mixture into a selected collection element;
   c. means for cleaning to remove residue from within the means for channeling and the conduit, wherein the means for channeling and the means for cleaning comprise a Venturi-type eductor having a motive fluid inlet, a suction inlet, and an outlet; and
   d. a sweep fluid reservoir coupled to the suction inlet to deliver sweep fluid through the suction inlet to the outlet and a motive fluid reservoir coupled to the motive fluid inlet to deliver motive fluid through the motive fluid inlet to the outlet, forming suction within the suction inlet.

2. The device of claim 1, wherein the collection element comprises one or more of the following: a filter, a vessel.

3. A device for sampling of a mixture of ultrafine particles within a moving gas stream, comprising:
   a. a suction generator, configurable to separate by suction and to entrain with a motive fluid, forming an output mixture, a portion of a gas stream containing a plurality of ultrafine particles, wherein the suction generator is a Venturi-type eductor having a motive fluid inlet, a suction inlet, and an outlet;
   b. a conduit structure coupled with the suction generator to channel the output mixture;
   c. at least one sample collection element configurable to accept a selected portion of the output mixture, and coupled with the suction generator via the conduit structure;
   d. a sweep fluid reservoir coupled to the suction inlet; and
   e. a motive fluid reservoir coupled to the motive fluid inlet, wherein the sweep fluid reservoir is configured to deliver sweep fluid through the suction inlet to the outlet and the motive fluid reservoir is configured to deliver motive fluid through the motive fluid inlet to the outlet, forming suction within the suction inlet.

4. The device of claim 3, wherein the sample collection element comprises one or more of the following: a filter, a vessel.

5. An apparatus for separating a portion of a moving mixture of ultrafine particles within a gas stream, comprising:
   a. a suction generator configured to entrain a particle-containing portion of a moving mixture within a motive fluid to form an output mixture, wherein the suction generator comprises a Venturi-type eductor having a motive fluid inlet, a suction inlet, and the outlet;
   b. a sweep fluid reservoir coupled with the suction inlet and configured to deliver a sweep fluid therethrough;
   c. a motive fluid reservoir coupled with the motive fluid inlet; and
   d. one or more collection elements removably coupled with the outlet to receive selected portions of the output mixture, wherein the suction generator is configured to allow removal by the sweep fluid and by the output mixture, of a residue from therewithin, further wherein the sweep fluid reservoir is configured to deliver the sweep fluid through the suction inlet to the outlet and the motive fluid reservoir is configured to deliver the motive fluid through the motive fluid inlet to the outlet, forming suction within the suction inlet.

6. The apparatus of claim 5, wherein the motive fluid reservoir and the sweep fluid reservoir are configured to irreversibly deliver their respective fluids.

7. The apparatus of claim 5, wherein the residue is a residue deposited from a prior output mixture during a prior use.

8. The apparatus of claim 5, wherein one or more of the collection elements comprises one or more of the following: a filter, a vessel.

9. An apparatus for separating a portion of a moving mixture of ultrafine particles within a gas stream, comprising:
   a. a Venturi-type eductor valve having a motive fluid inlet, a suction inlet, and an outlet configured to form a negative pressure stream biased from the suction inlet to the outlet and capable of entraining a portion of the moving mixture of ultrafine particles within a gas stream when a motive fluid is flowed from the motive fluid inlet to the outlet, wherein the suction inlet is configurable to communicate with the moving mixture of ultrafine particles within a gas stream;
   b. a motive fluid reservoir configured to irreversibly deliver motive fluid through the motive fluid inlet;
   c. a sweep fluid reservoir configured to irreversibly deliver sweep fluid through the suction inlet to the outlet;
   d. a conduit structure coupled with the outlet and configured to allow the removal of a residue therefrom by the output mixture and by the sweep fluid; and
   e. one or more collection elements sealably coupled with the conduit structure to accept delivery of at least a portion of the output mixture, wherein at least one of the collection elements is a bulk collection chamber coupled with the conduit structure via a one way valve biased to allow flow only from the conduit structure into the bulk collection chamber.

10. A method of sampling powder from a gas stream containing ultrafine particles, comprising:
    a. separating a portion of gas containing a target powder from the gas stream by suction to form a mixture of a motive fluid with the target powder entrained therein;
    b. directing a first portion of the mixture through a conduit structure for a period of time sufficient to substantially clean the conduit structure;
    c. directing a second portion of the mixture through the conduit structure into a collection element after the period of time; and
    d. flowing a sweep fluid through the conduit structure to maintain substantial entrainment of the target powder, wherein the suction is provided by a negative pressure stream formed by flowing the motive fluid through a Venturi-type eductor having a motive fluid inlet, a suction inlet, and an outlet; further wherein a sweep fluid is delivered through the suction inlet to the outlet.

11. The method of claim 10, further comprising repeating the steps of 'flowing' through the step of 'directing a second portion'.

12. The method of claim 10, wherein the collection element comprises one or more of the following: a filter, a vessel.

13. A process for achieving high purity sampling of at least two mixtures from a single source, comprising:

a. flowing a motive fluid through a Venturi-type eductor valve to form a negative pressure stream;

b. applying the negative pressure stream to a first gas stream to separate a portion thereof and entrain it into a first target mixture, the gas stream containing a first target powder and originating from a source;

c. directing the first target mixture through a conduit network into a first collection element;

d. flowing a sweep gas through the Venturi-type eductor valve, without forming a negative pressure stream, and through the conduit network to remove at least a portion of remaining first target mixture therefrom;

e. flowing a motive fluid through a Venturi-type eductor valve to form a negative pressure stream;

f. applying the negative pressure stream to a second gas stream to separate a portion thereof and entrain it into a second target mixture, the gas stream containing a second target powder and originating from the source;

g. flowing a portion of the second target mixture through the conduit network for a time sufficient to substantially clean the conduit network of the remaining first target mixture; and h. directing a further portion of the second target mixture through the conduit network into a second collection element, wherein the steps of 'flowing a motive fluid' and of 'flowing a sweep gas' are coordinated to maintain substantial entrainment of the first and the second target powders throughout the conduit network for the duration of the process.

14. The process of claim 13, wherein the first collection element and the second collection element comprises one or more of the following: a filter, a vessel.

* * * * *